United States Patent
Olive et al.

(10) Patent No.: US 9,896,507 B2
(45) Date of Patent: Feb. 20, 2018

(54) BTLA ANTIBODIES AND USES THEREOF

(71) Applicants: Universite d'Aix Marseille, Marseilles (FR); INSERM (Institut National de la Sante et de la Recherche Medicale), Paris (FR)

(72) Inventors: Daniel Olive, Marseilles (FR); Francoise Gondois-Rey, Marseilles (FR); Nacer-Eddine Serriari, Amiens (FR); Sonia Pastor, Marseilles (FR)

(73) Assignees: Université d'Aix Marseille, Marseille (FR); INSERM (Institut National de la Santé et de la Recherche Médicale), Paris (FR)

(*) Notice: Subject to any disclaimer, the term of this patent is extended or adjusted under 35 U.S.C. 154(b) by 419 days.

(21) Appl. No.: 14/550,429

(22) Filed: Nov. 21, 2014

(65) Prior Publication Data
US 2015/0147344 A1 May 28, 2015

Related U.S. Application Data

(62) Division of application No. 13/255,977, filed as application No. PCT/EP2010/053356 on Mar. 16, 2010, now abandoned.

(30) Foreign Application Priority Data

Mar. 17, 2009 (EP) .................................. 09305246

(51) Int. Cl.
*C07K 16/28* (2006.01)
*A61K 39/395* (2006.01)
*A61K 39/00* (2006.01)

(52) U.S. Cl.
CPC ...... *C07K 16/2818* (2013.01); *A61K 39/3955* (2013.01); *C07K 16/2827* (2013.01); *C07K 16/2878* (2013.01); *A61K 2039/505* (2013.01); *C07K 2317/54* (2013.01); *C07K 2317/55* (2013.01); *C07K 2317/565* (2013.01); *C07K 2317/73* (2013.01); *C07K 2317/74* (2013.01)

(58) Field of Classification Search
None
See application file for complete search history.

(56) References Cited

U.S. PATENT DOCUMENTS

| 8,580,259 | B2 | 11/2013 | Korman et al. |
| 9,605,070 | B2 * | 3/2017 | Sabatos-Peyton . A61K 39/3955 |
| 9,683,048 | B2 * | 6/2017 | Freeman ............ C07K 16/2896 |
| 2004/0175380 | A1 | 9/2004 | Allison et al. |
| 2010/0172900 | A1 | 7/2010 | Korman et al. |

FOREIGN PATENT DOCUMENTS

| WO | 2007/001459 | 1/2007 |
| WO | 2008/076560 | 6/2008 |

OTHER PUBLICATIONS

Romero et al. Sci Transl Med. (2016) 8: 334ps9, 8 pages.*
Pasero et al. Immunology Letters (2013) 151: 71-75.*
Gonzalez et al., "A coreceptor interaction between the CD28 and TNF receptor family members B and T lymphocyte attenuator and herpesvirus entry mediator," Proc. Natl. Acad. Sci. USA, 102(4):1116-1121 (2005) XP002534826.
International Search Report in PCT/EP2010/53356, dated Aug. 13, 2010.
M'Hidi et al., "High Expression of the Inhibitory Receptor BTLA in T-Follicular Helper Cells and in B-Cell Small Lymphocytic Lymphoma/Chronic Lymphocytic Leukemia," Am. J. Clin. Pathol., 132(4):589-596 (2009) XP9135450.
Olive, "Lymphocyte coreceptors," Medecine Sciences, 22(12):1069-1074 (2006) XP9135449.
Ware, "Targeting lymphocyte activation through the lymphotoxin and LIGHT pathways," Immunol. Rev., 223 (1):186-201 (2008) XP002532007.

* cited by examiner

*Primary Examiner* — Ilia Ouspenski
(74) *Attorney, Agent, or Firm* — Whitham, Curtis & Cook, P.C.

(57) ABSTRACT

The invention relates to BTLA antibodies that block BTLA-HVEM interaction and uses thereof.

4 Claims, 12 Drawing Sheets

Figure 1A:
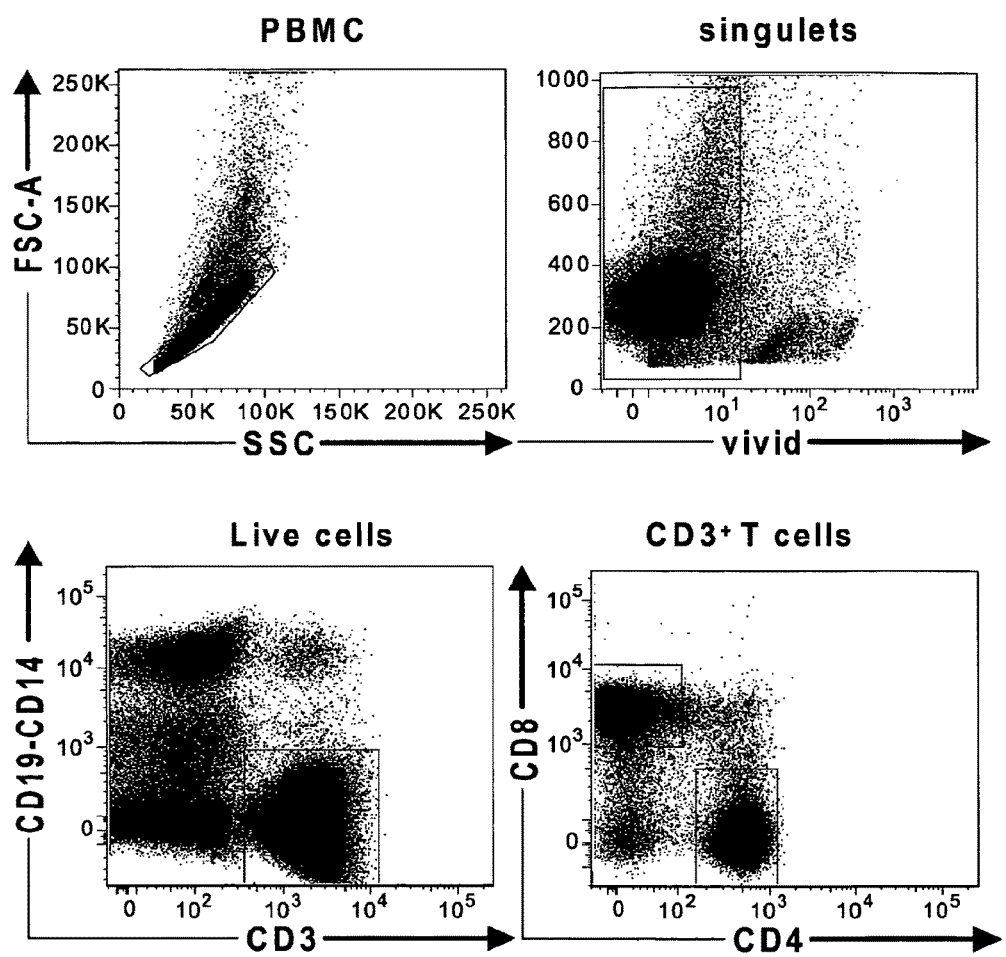

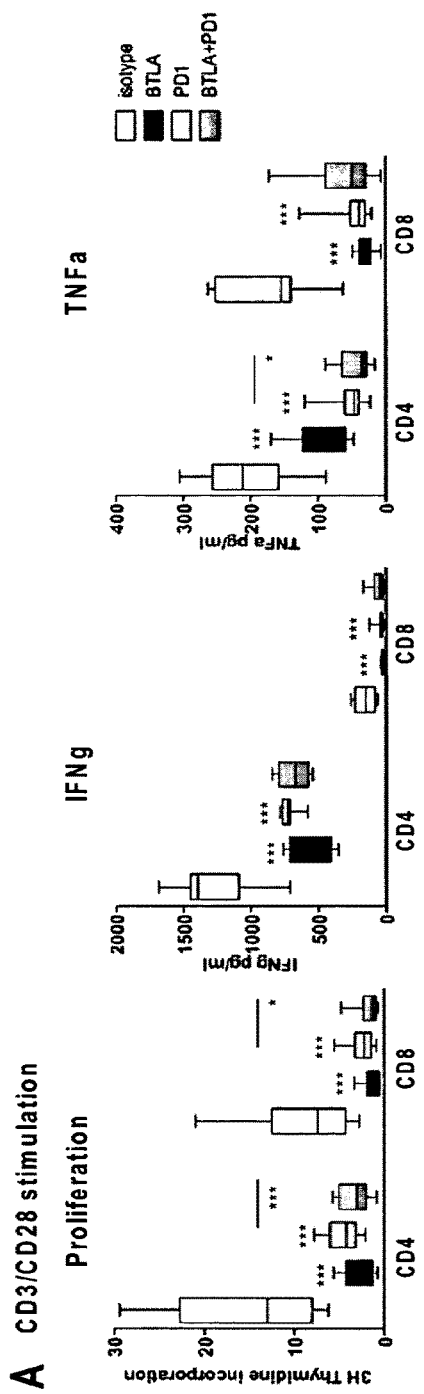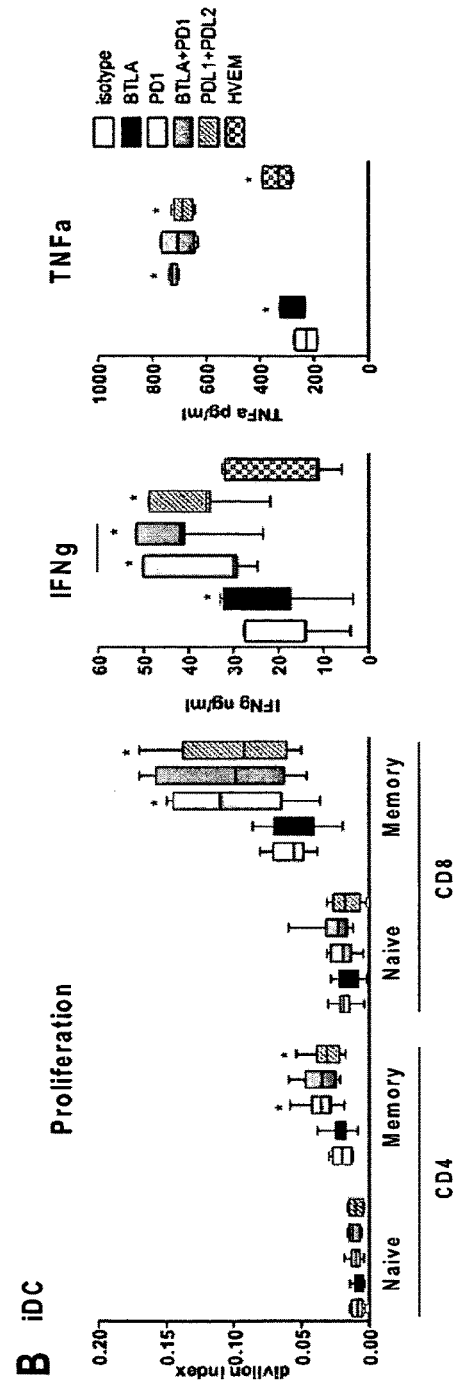
FIG. 2A
FIG. 2B

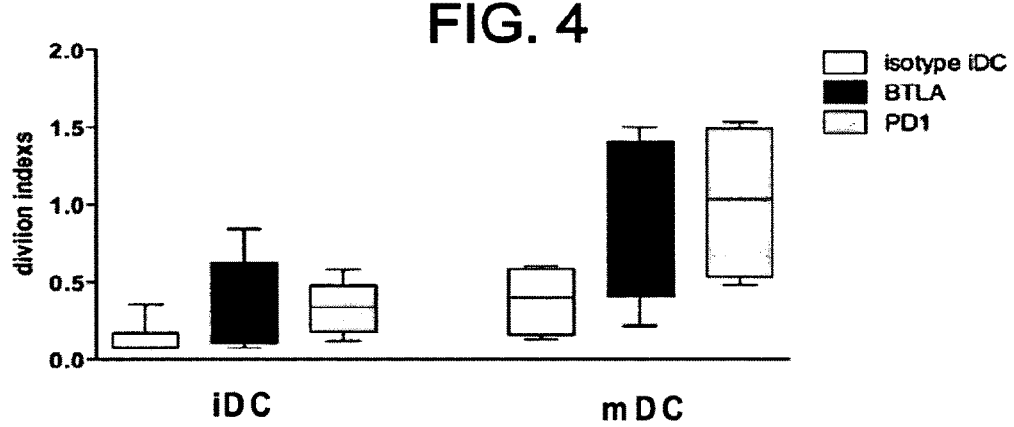

//BTLA ANTIBODIES AND USES THEREOF

The present application is filed as a divisional of U.S. patent application Ser. No. 13/255,977, which was filed Nov. 28, 2011, which was filed pursuant to 35 U.S.C. 371 as a U.S. National Phase application of International Patent Application No. PCT/EP2010/053356, which was filed Mar. 16, 2010, claiming the benefit of priority to European Patent Application No. 09305246.2, which was filed on Mar. 17, 2009. The entire text of the aforementioned applications is incorporated herein by reference in its entirety.

FIELD OF THE INVENTION

The invention relates to BTLA antibodies that blocks BTLA-HVEM interaction and uses thereof.

BACKGROUND OF THE INVENTION

Co-receptor signalling is an important mechanism for coordinating and tightly regulating immune responses. The usual scheme of activation of $\alpha\beta$ T cells relies on positive signals given by peptide antigens presented by HLA class I or II. Co-receptor signals will either increase or prevent this activation.

Among the negative signalling molecules, those belonging to CD28/B7 families are by far the most studied. Three members of this family have been described: CTL-associated antigen-4 (CTLA-4), programmed death-1 (PD-1) and B and T lymphocyte attenuator (BTLA). They all play a role in the control of tolerance. They provide negative signals that limit, terminate and/or attenuate immune responses.

BTLA (CD272) is the most recently described member of the CD28 family, it was first identified as a transcript highly specific to T helper 1 ($T_H1$) cells but was later shown to be expressed by thymocytes. Initially, B7x was suggested as a ligand of BTLA but it has been recently confirmed that BTLA interacts with HVEM (herpes virus-entry mediator), a member of the tumour-necrosis factor receptor (TNFR) family (Gonzalez et al., Proc. Natl. Acad. Sci. USA, 2005, 102: 1116-21). The interaction of BTLA, which belongs to the CD28 family of the immunoglobulin superfamily, and HVEM, a costimulatory tumor-necrosis factor (TNF) receptor (TNFR), is quite unique in that it defines a cross talk between these two families of receptors.

BTLA is constitutively expressed in both B and T cells. Like PD-1, BTLA contains a membrane proximal immunoreceptor tyrosine-based inhibitory motif (ITIM) and membrane distal immunoreceptor tyrosine-based switch motif (ITSM). Disruption of either the ITIM or ITSM abrogated the ability of BTLA to recruit either SHP1 or SHP2, suggesting that BTLA recruits SHP1 and SHP2 in a manner distinct from PD-1 and both tyrosine motifs are required to block T cell activation.

The BTLA cytoplasmic tail also contains a third conserved tyrosine-containing motif within the cytoplasmic domain, similar in sequence to a Grb-2 recruitment site (YXN). Gavrieli et al recently showed that a phosphorylated peptide containing this BTLA N-terminal tyrosine motif can interact with GRB2 and the p85 subunit of PI3K in vitro, although the functional effects of this interaction remain unexplored in vivo (Gavrieli et al., Bioochem. Biophysi Res Commun, 2003, 312, 1236-43).

To date, no satisfactory approach has been proven to induce potent immune responses against vaccines, especially in cancer patients. Methods have yet to be devised to overcome the immunosuppressive mechanisms observed in cancer patients, and during chronic infections.

SUMMARY OF THE INVENTION

The invention relates to a BTLA antibody that blocks BTLA-HVEM interaction for the use in a method for treatment of a human or animal body by therapy.

The invention relates to a BTLA antibody that blocks BTLA-HVEM interaction for the treatment of a cancer or a chronic infection.

The invention relates to a vaccine for the treatment of a cancer or a chronic infection comprising a BTLA antibody that blocks BTLA-HVEM interaction.

The invention relates to a kit for the treatment of a cancer or a chronic infection comprising:
a) a BTLA antibody that blocks BTLA-HVEM interaction; and
b) a vaccine for the treatment of a cancer or a chronic infection.

The present invention also relates to a BTLA antibody (BTLA8.2) which is obtainable from the hybridoma accessible under CNCM deposit number I-4123.

The invention also relates to a BTLA antibody which comprises the CDRs of BTLA8.2.

The invention relates to BTLA8.2 or a derivative thereof for the use in a method for treatment of the human or animal body by therapy.

The invention relates to BTLA8.2 or a derivative thereof for the treatment of a cancer or a chronic infection.

DETAILED DESCRIPTION OF THE INVENTION

Figures

Figure 1B:
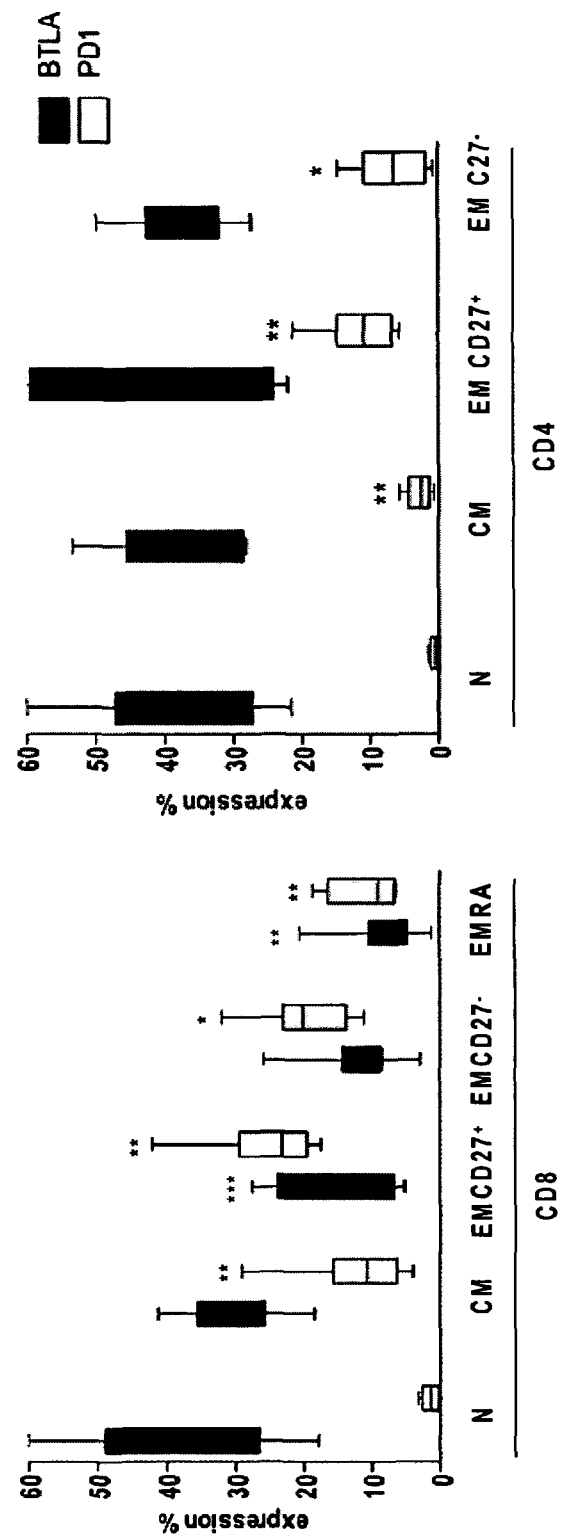
Figure 1C:
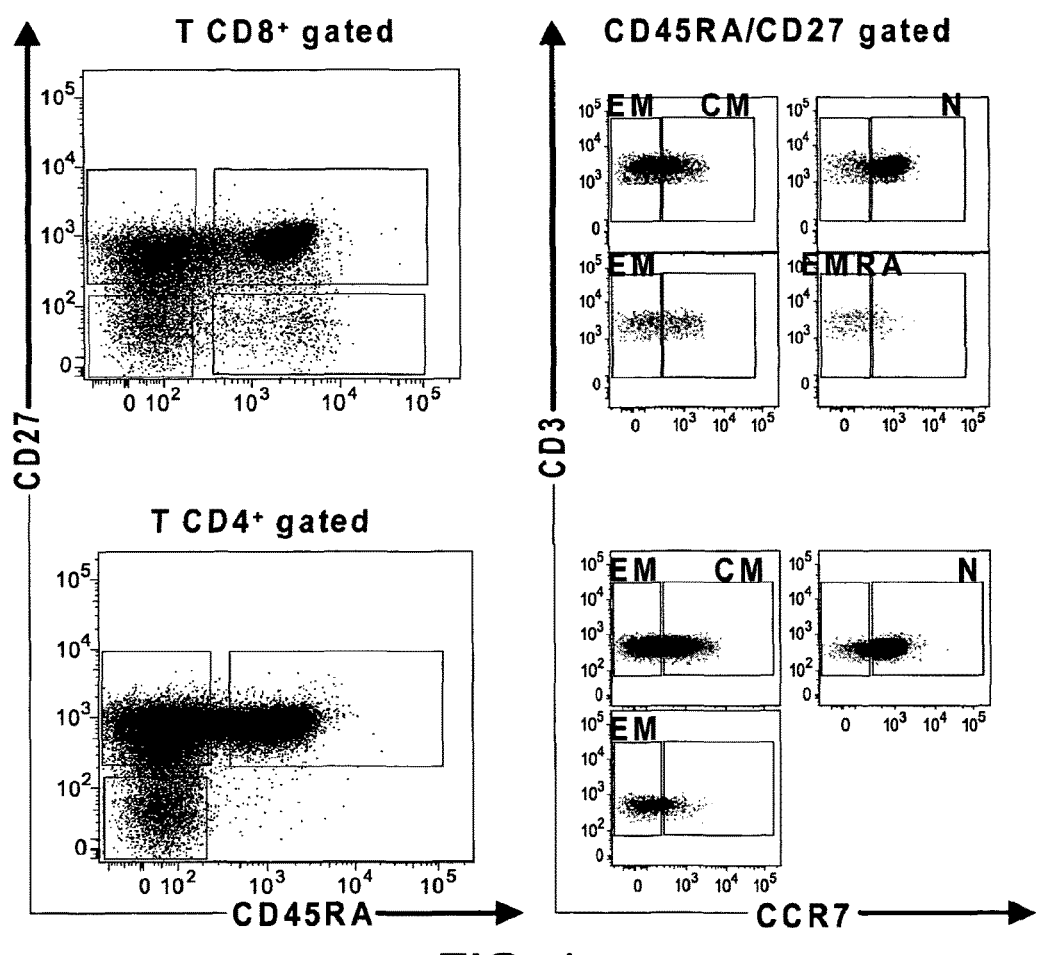

FIGS. 1A, 1B and 1C: BTLA is Down Regulated During the Course of CD8 but not CD4 T Cell Differentiation CD8 and CD4 T cells were analysed by flow cytometry from healthy volunteers.

A—gating strategy for identification of T cells subsets of differentiation. After exclusion of dead cells (vivid+) and CD14+CD19+ cells, B—BTLA and PD1 expression on T-CD8 and T-CD4 subsets of differentiation healthy blood donors. (n=12) The horizontal bar indicates the median and minimum and maximum values are shown. Percentages of BTLA and PD1 positive cells are shown within each subset. Each population is compared to the previous subset of differentiation and the significant P values are indicated as *: $p>0.05$, : $0.001<p<0.01$, * or $p<0.001$ (Wilcoxon test). Statistics were calculated in Prism5.

C— T lymphocytes were gated into $CD3^+CD4^+$ and $CD3^+CD8^+$ populations. Cells are first analyzed for expression of CD45RA and CD27, and then for expression of CCR7. Naives T lymphocytes (N) $CD45RA^+CD27^+CCR7^+$, Central Memory (CM) $CD45RA^-CD27^+CCR7^+$, Effector Memory (EM) $CD45RA^-CD27^+CCR7^-$ and $CD45RA^-CD27^-CCR7^-$, Effector Memory $RA^+CD45RA^+CD27^-CCR7^-$.

Figure 2C:
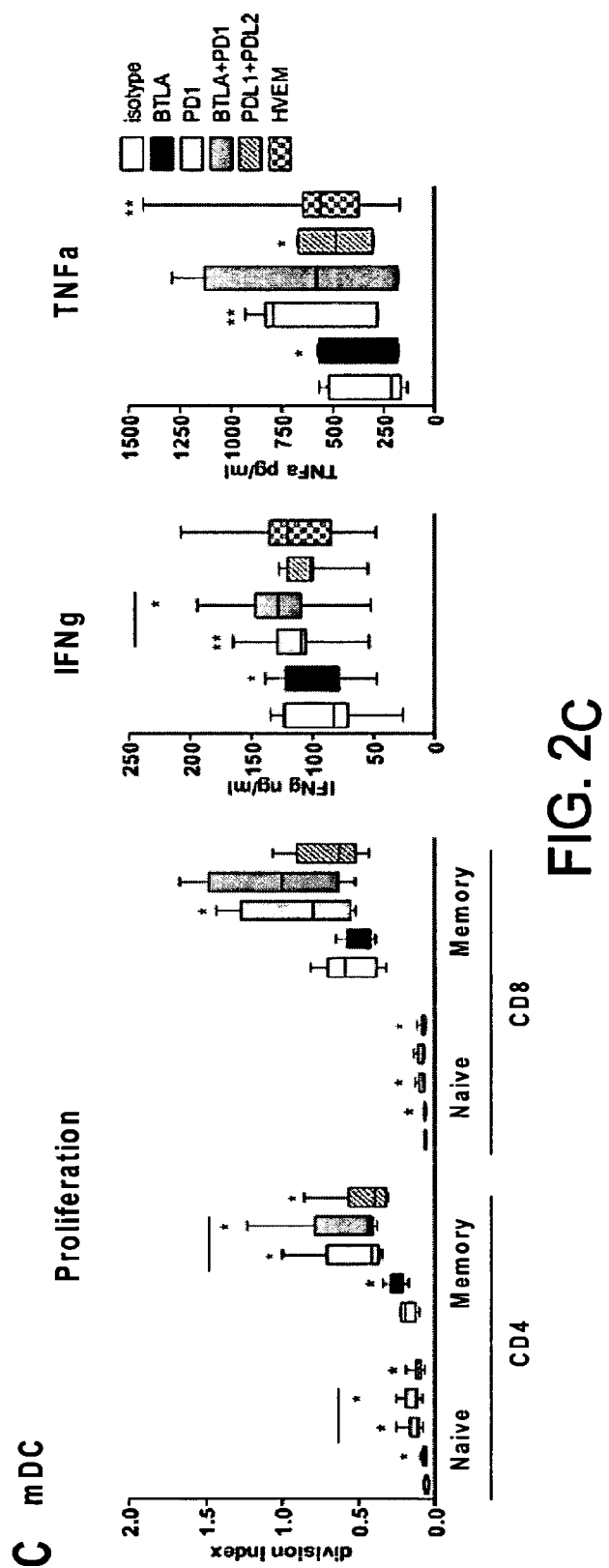

FIGS. 2A, 2B and 2C: Inhibition of T Cells Activation by BTLA and PD1 mAbs.

Purified T CD4 and T CD8 lymphocytes are stimulated by:

A—beads coated with CD3-CD28 and different combinations of mAb directed against BTLA, PD1, PDL-1+PDL- 2, and HVEM. Proliferation is measured by 3H thymidine incorporation. IFNg and TNFa release in supernatants are quantified by ELISA.

B—co-culture with immature allogenic DC in the presence of BTLA, PD1, PDL1+PDL2, or HVEM mAb C—co-culture with mature allogenic DC in the presence of BTLA, PD1, PDL1+PDL2, or HVEM mAb.

For DC stimulation, proliferation is measured by the division index on day 5 after a CFSE labelling into the naive and the memory T CD4 or T CD8 cells sub-populations. The division index is calculated with the proliferation tool of FlowJo 8-8-3. The p value indicated are calculated between each condition and the isotype control, except for the BTLA+PD1 condition which is always compared to PD1 alone.

Figure 3A:
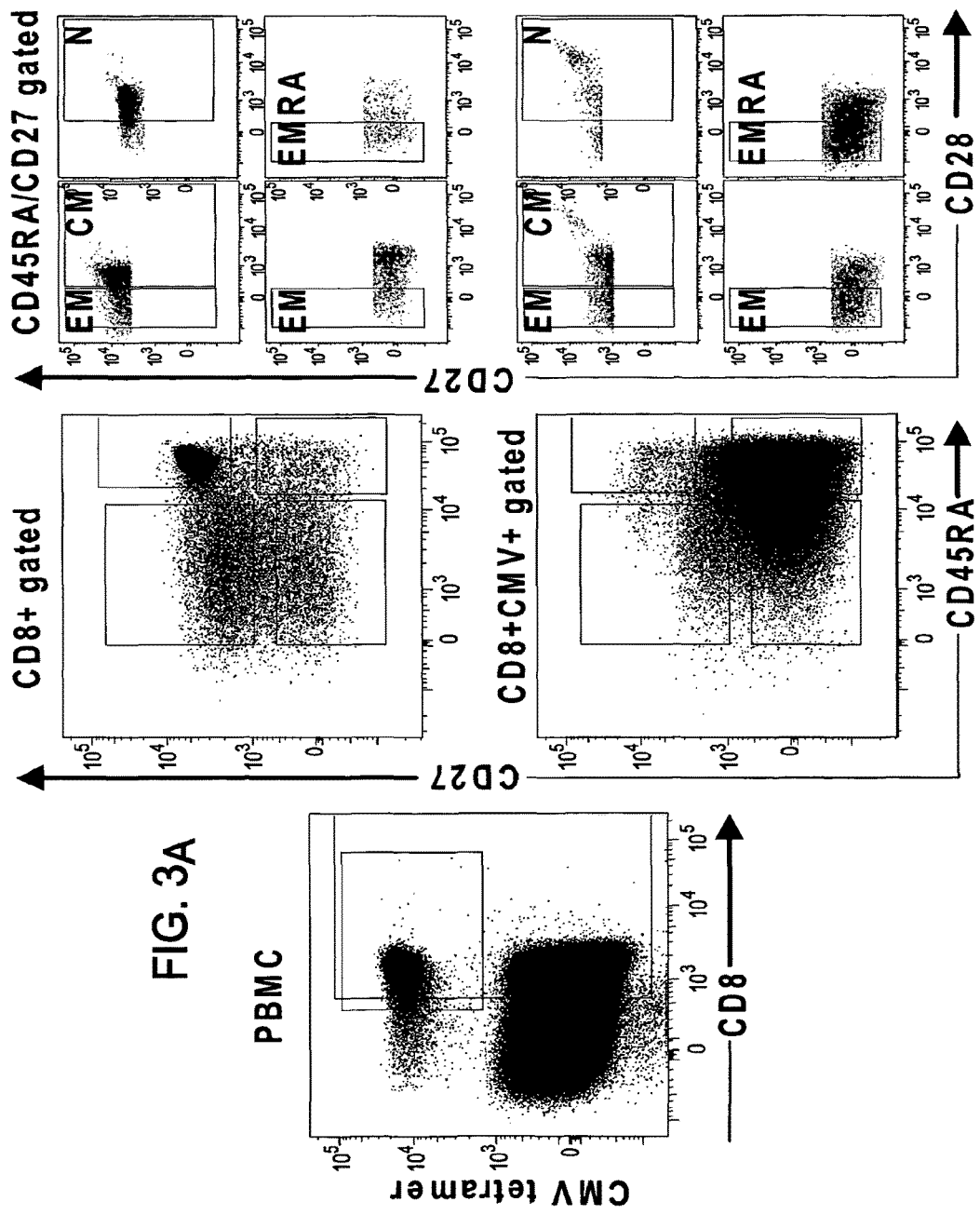
Figure 3B:
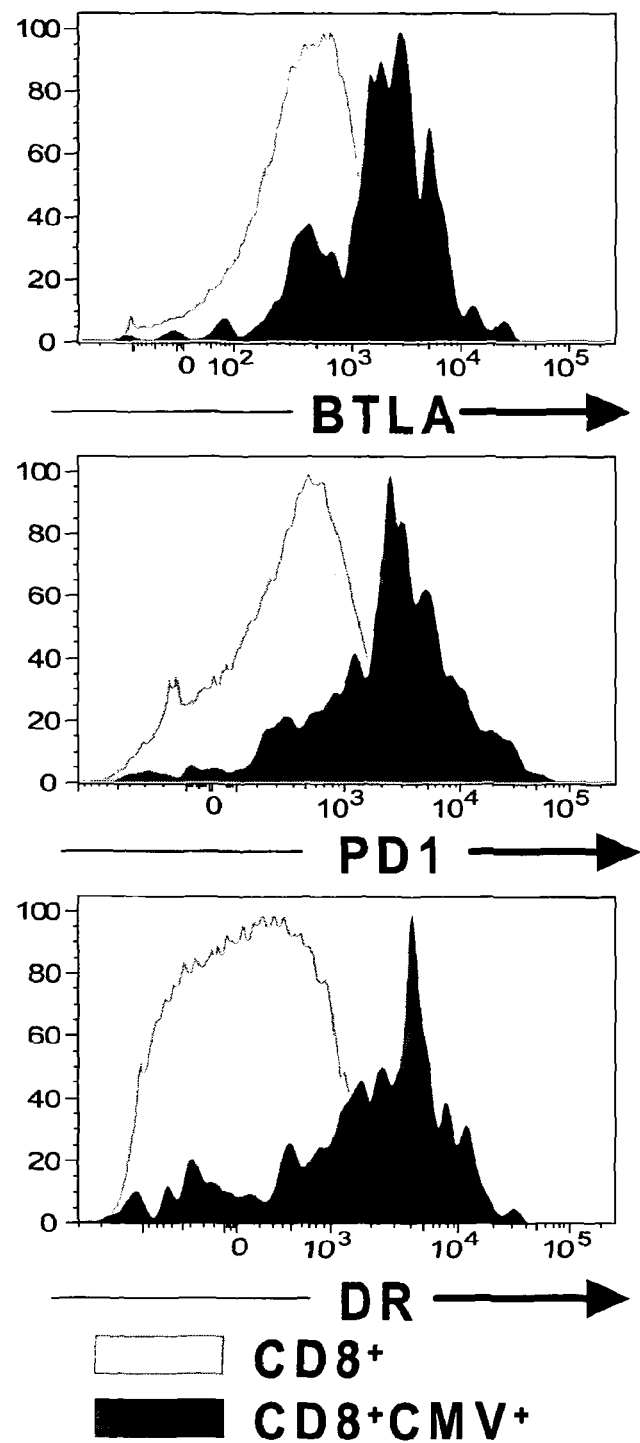
Figure 3C:
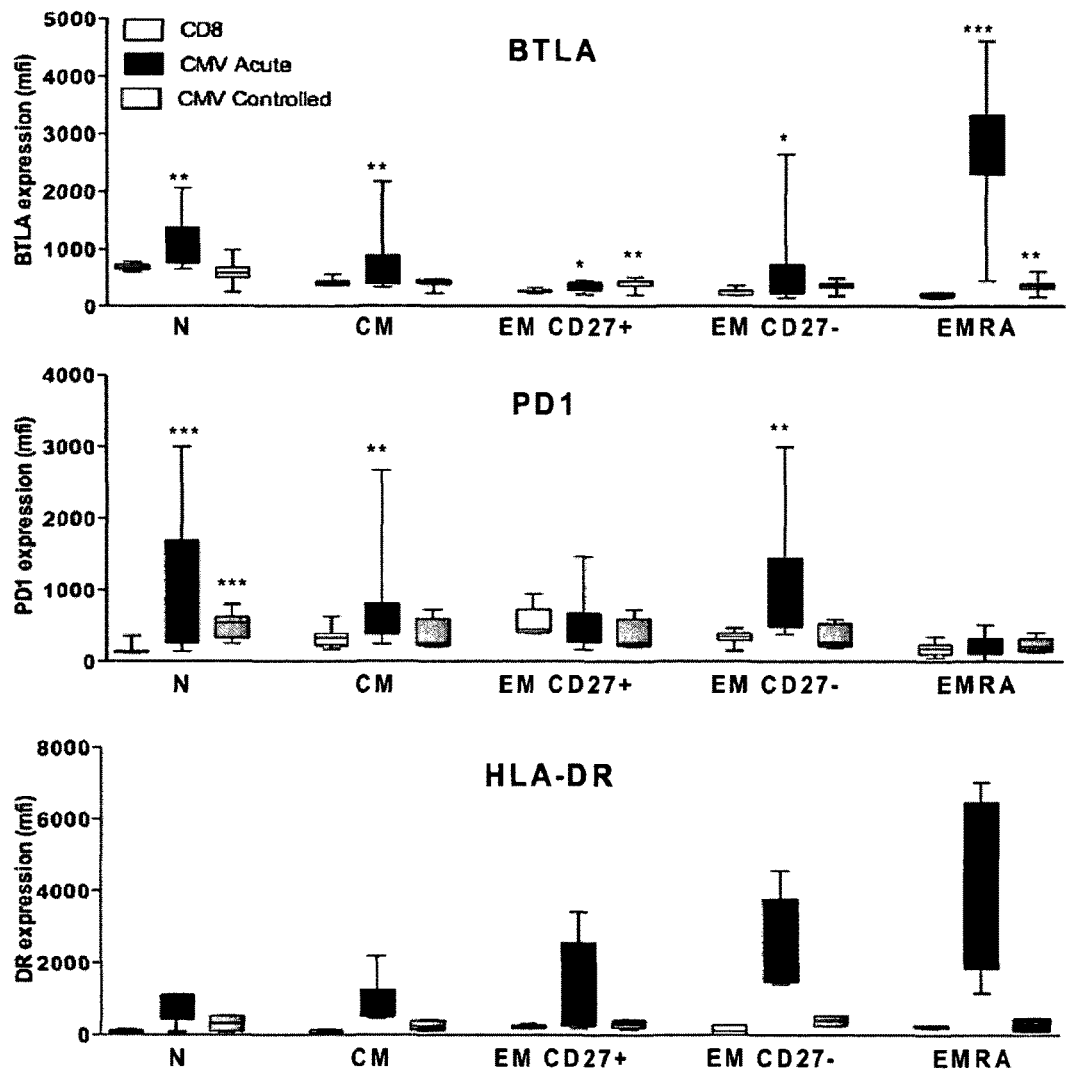

FIGS. 3A, 3B and 3C: BTLA and PD1 Expression During CMV Specific Activation

BTLA and PD1 expression were analyzed during CMV re-burst in 2 transplanted patients. The acute and controlled phases of infection were defined according to CMV-PCR. Acute represents pooled data from samples taken during the viremia (i.e week 3 to 6 for patient 1 and week 5 to 9 for patient 2), controlled corresponds to samples taken when viremia was negative (up to week 145 for patient 1 and week 51 for patient 2).

A—Gating strategy for identification of CD8 subsets of differentiation. CD8 positive and CD8 CMV positive cells were gated from alive lymphocytes. Population were then defined on CD45RA and CD27 expression, and further sub-divided on CD28 expression. Naive cells: CD45RA$^+$CD27$^+$, CD28$^+$, Central Memory (CM): CD45RA$^-$CD27$^+$CD28$^+$, Effector Memory CD27$^+$:CD45RA$^-$CD27$^+$, CD28$^-$, Effector Memory CD27–: CD45RA$^-$CD27$^-$CD28$^-$ and Effector memory RA$^+$ (EMRA): CD45RA$^+$CD27$^-$CD28$^-$.

B—BTLA, PD1 and HLA-DR expression in total CD8 and CMV tetramer positive CD8 cells at week 5 after transplantation.

C—BTLA, PD1 and HLA-DR expression on CD8 and CMV tetramer positive CD8 cells subsets of differentiation of 2 patients analyzed with 3 different tetramers of CMV. Expression on total CD8 was measured before CMV re-burst, acute and controlled phases were defined according to viremia. Median, minimum and maximum values are shown. Each population is compared to the previous subset of differentiation *: p>0.05, : 0.001≤p≤0.01, *: p<0.001 (Wilcoxon test). Statistics were calculated in Prism5.

FIG. 4: Inhibition of CMV Specific Activation by BTLA and PD1 mAb

Mature or immature DC were stimulated by pp65 CMV peptide, and co-cultivated with purified T lymphocytes in the presence of BTLA or PD1 mAb. Activation of total cells, CD8 or CD8+CMV+ T lymphocytes is analyzed by proliferation measured 7 days after a CFSE labelling. The division index is calculated with the proliferation tool of FlowJo.

Figure 5:
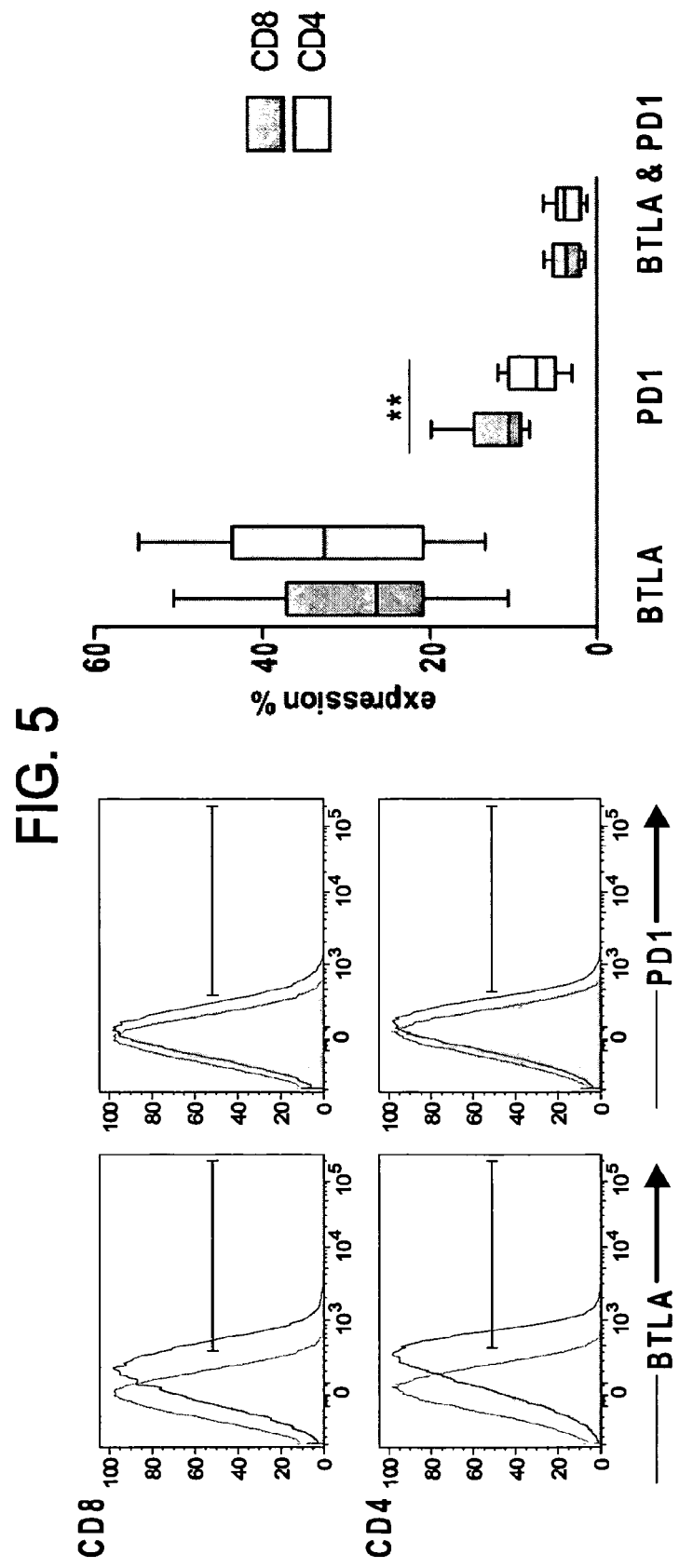

FIG. 5: Co-Expression of BTLA and PD1 in T CD4 and T CD8 Lymphocytes of Healthy Blood Donor.

Figure 6:
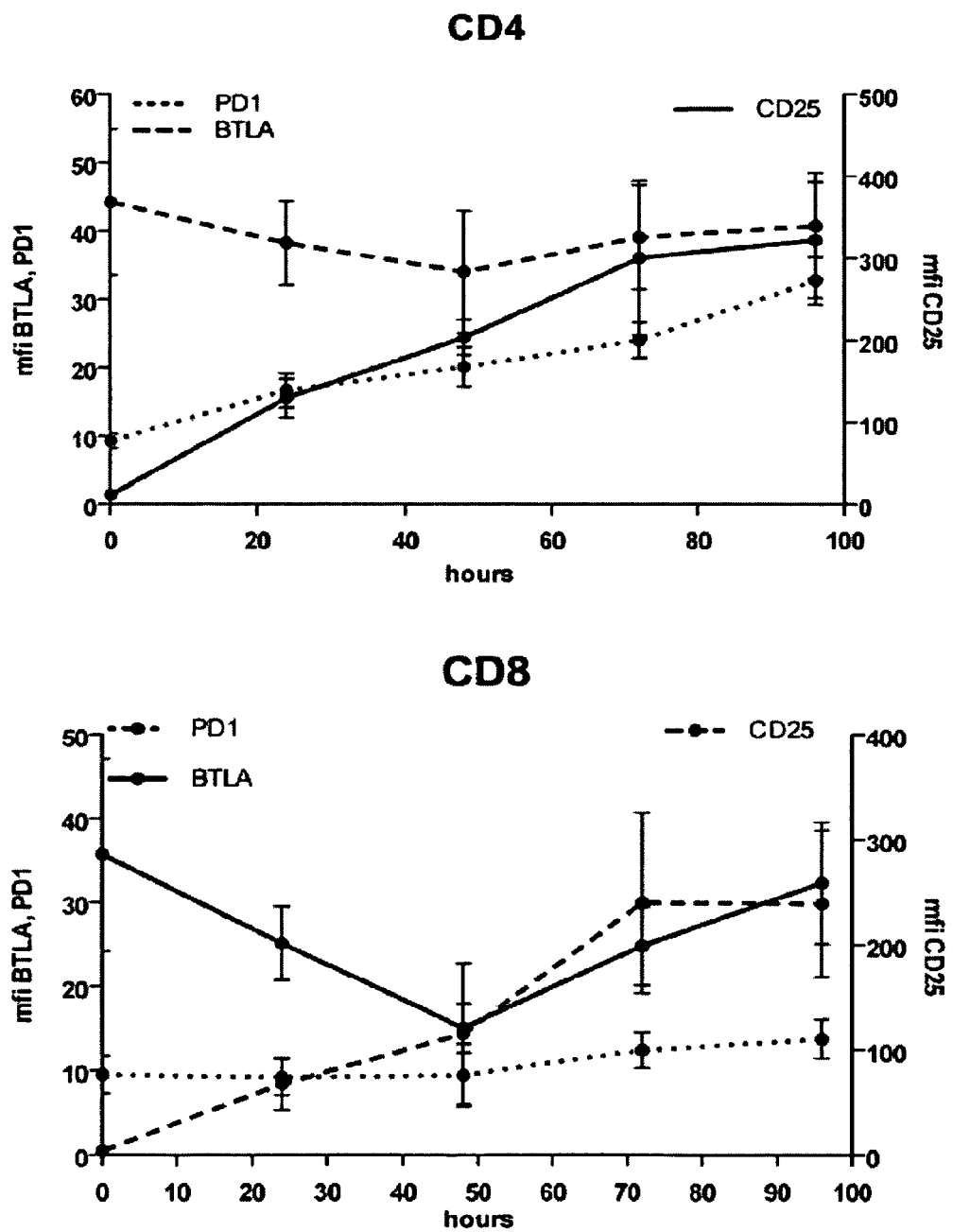

FIG. 6: BTLA and PD1 Expression after In Vitro Activation with CD3/CD28 mAb

Expression is expressed as the median fluorescence intensity (mfi) of each marker over the time. CD25 expression is measured as a marker of activation.

Figure 7:
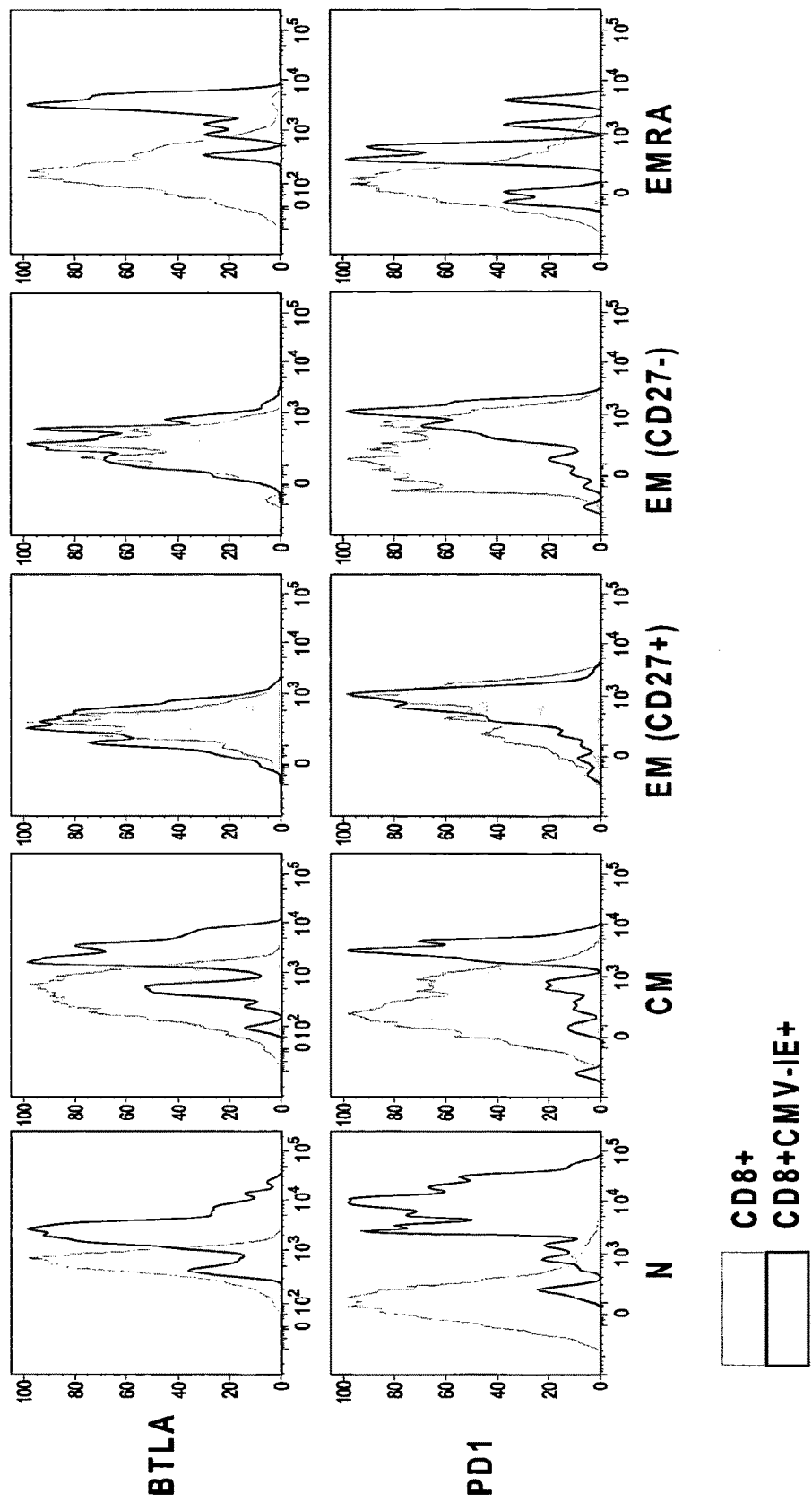

FIG. 7: BTLA and PD1 Expression in CD8+CMV+ T Lymphocytes Differentiation Subsets in Patients.

Histograms show BTLA and PD1 expression in a patient in T CD8 subsets of differentiation before CMV infection, and in CD8+CMV-IE+ subsets of differentiation during acute infection (week 6).

DEFINITIONS

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments or derivatives. Antibody fragments include but are not limited to Fv, Fab, F(ab')$_2$, Fab', dsFv, scFv, sc(Fv)$_2$ and diabodies.

In natural antibodies, two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The terms "chimeric antibody" refer to a genetically engineered fusion of parts of an animal antibody, typically a mouse antibody, with parts of a human antibody. Generally, chimeric antibodies contain approximately 33% mouse protein and 67% human protein. Developed to reduce the Human Anti-animal Antibodies response elicited by animal antibodies, they combine the specificity of the animal antibody with the efficient human immune system interaction of a human antibody.

According to the invention, the term "humanized antibody" refers to an antibody having variable region framework and constant regions from a human antibody but retains the CDRs of the animal antibody.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')$_2$" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by proteolytic cleavage of an IgG with the protease, papain.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)$_2$.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to a polypeptide (i.e. an antibody according to the invention) or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

In the context of the invention, the term "treating" or "treatment", as used herein, means reversing, alleviating, inhibiting the progress of, or preventing the disorder or condition to which such term applies, or one or more symptoms of such disorder or condition. A "therapeutically effective amount" is intended for a minimal amount of active agent which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

As used herein, the term "prevention" refers to preventing the disease or condition from occurring in a subject which has not yet been diagnosed as having it.

As used herein, the term "subject" denotes a mammal, such as a rodent, a feline, a canine, and a primate. Preferably a subject according to the invention is a human.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The inventors have deposited a murine BTLA antibody (BTLA8.2) producing hybridoma at the Collection Nationale de Cultures de Microorganismes (CNCM, Institut Pasteur, 25 rue du Docteur Roux, 75724 Paris Cedex 15, France), in accordance with the terms of Budapest Treaty, on Feb. 4, 2009. The deposited hybridoma has CNCM deposit number I-4123.

"BTLA8.2" refers to an isolated BTLA antibody which is obtainable from the hybridoma accessible under CNCM deposit number I-4123

The expression "a derivative of BTLA8.2" refers to a BTLA antibody which comprises the 6 CDRs of BTLA8.2 and its function conservative fragments.

Antibodies of the Invention and Nucleic Acids Encoding them

The inventors have demonstrated that a BTLA antibody that blocks BTLA-HVEM interaction may be used to overcome the immunosuppressive mechanisms mediated by HVEM observed in cancer patients and during chronic infections.

The invention relates to a BTLA antibody that blocks BTLA-HVEM interaction for the use in a method for treatment of the human or animal body by therapy.

The present invention also relates to an isolated BTLA antibody (BTLA8.2) which is obtainable from the hybridoma accessible under CNCM deposit number I-4123.

The present invention relates to the hybridoma accessible under CNCM deposit number I-4123.

The invention relates to an antibody which comprises the 6 CDRs of BTLA8.2.

In another embodiment, the invention relates to a derivative of BTLA8.2 which comprises the VL chain and the VH chain of BTLA8.2.

In another embodiment, the invention relates to a derivative of BTLA8.2 which is a chimeric antibody, which comprises the variable domains of BTLA8.2.

In an embodiment, an antibody of the invention is a monoclonal antibody.

In an embodiment, an antibody of the invention is a chimeric antibody.

In an embodiment, an antibody of the invention is a humanized antibody.

A further embodiment of the invention relates to a nucleic acid sequence encoding an antibody of the invention.

In a particular embodiment, the invention relates to a nucleic acid sequence encoding the VH domain or the VL domain of an antibody of the invention.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40, LTR promoter and enhancer of Moloney mouse leukemia virus, promoter and enhancer of immunoglobulin H chain and the like.

Any expression vector for animal cell can be used, so long as a gene encoding the human antibody C region can be inserted and expressed. Examples of suitable vectors include pAGE107, pAGE103, pHSG274, pKCR, pSG1 beta d2-4- and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective, rat YB2/3HL.P2.G11.16Ag.20 cell (ATCC CRL1662, hereinafter referred to as "YB2/0 cell"), and the like.

The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the invention.

Methods of Producing Antibodies of the Invention

Antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In particular, the invention further relates to a method of producing an antibody of the invention, which method comprises the steps consisting of: (i) culturing a transformed host cell according to the invention under conditions suitable to allow expression of said antibody; and (ii) recovering the expressed antibody.

In another particular embodiment, the method comprises the steps of:

(i) culturing the hybridoma deposited as CNCM I-4123 under conditions suitable to allow expression of the antibody; and (ii) recovering the expressed antibody.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (See patent documents U.S. Pat. No. 5,202,238; and U.S. Pat. No. 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Examples of tandem type humanized antibody expression vector include pKANTEX93 (WO 97/10354), pEE18 and the like.

Methods for producing humanized antibodies based on conventional recombinant DNA and gene transfection techniques are well known in the art. Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519, 596), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with PD-1 with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')$_2$ of the present invention can be obtained treating an antibody which specifically reacts with BTLA8.2 with a protease, pepsin. Also, the F(ab')$_2$ can be produced by binding Fab' described below via a thioether bond or a disulfide bond.

The Fab' of the present invention can be obtained treating F(ab')$_2$ which specifically reacts with human PD-1 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. No. 5,859,205; U.S. Pat. No. 5,585,089; U.S. Pat. No. 4,816,567; EP0173494).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. As proposed by Kyte and Doolittle, J Mol Biol 157:105-132, each amino acid has been assigned a hydropathic index on the basis of their hydrophobicity and charge characteristics; these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further embodiment of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Enzymatic cleavage of carbohydrate moieties on antibodies can be achieved by the use of a variety of endo- and exo-glycosidases.

Another type of covalent modification of the antibody comprises linking the antibody to one of a variety of non proteinaceous polymers, eg., polyethylene glycol, polypropylene glycol, or polyoxyalkylenes, in the manner set forth in U.S. Pat. No. 4,640,835; 4,496,689; 4,301,144; 4,670, 417; 4,791,192 or 4,179,337.

It may be also desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. J Exp Med. 1992 Oct. 1; 176(4):1191-5 and Shopes B. J. Immunol. 1992 May 1; 148(9):2918-22).

Therapeutic Uses of the Antibodies of the Invention

The invention relates to a BTLA antibody that blocks BTLA-HVEM interaction for the use in a method for treatment of the human or animal body by therapy.

The invention relates to a BTLA antibody that blocks BTLA-HVEM interaction for the treatment of a cancer or a chronic infection.

The invention relates to a vaccine for the treatment of a cancer or a chronic infection comprising a BTLA antibody that blocks BTLA-HVEM interaction.

The invention relates to a kit for the treatment of a cancer or a chronic infection comprising:
 a) a BTLA antibody that blocks BTLA-HVEM interaction; and
 b) a vaccine for the treatment of a cancer or a chronic infection.

The invention also relates to BTLA8.2 or a derivative thereof for the use in a method for treatment of the human or animal body by therapy. As said above, "a derivative of BTLA8.2" refers to a BTLA antibody which comprises the 6 CDRs of BTLA8.2 and its function conservative fragments.

The invention relates to BTLA8.2 or a derivative thereof for the treatment of a cancer or a chronic infection.

The invention also relates to a method for treating a cancer or a chronic infection wherein said method comprises the step of administering to a subject in need thereof a therapeutically effective amount of a BTLA antibody that blocks BTLA-HVEM interaction (e.g., BTLA8.2 or a derivative thereof).

Examples of cancers include, but are not limited to, hematological malignancies such as B-cell lymphoid neoplasm, T-cell lymphoid neoplasm, non-Hodgkin lymphoma (NHL), B-NHL, T-NHL, chronic lymphocytic leukemia (CLL), small lymphocytic lymphoma (SLL), mantle cell lymphoma (MCL), NK-cell lymphoid neoplasm and myeloid cell lineage neoplasm. Examples of non-hematological cancers include, but are not limited to, colon cancer, breast cancer, lung cancer, brain cancer, prostate cancer, head and neck cancer, pancreatic cancer, bladder cancer, colorectal cancer, bone cancer, cervical cancer, liver cancer, oral cancer, esophageal cancer, thyroid cancer, kidney cancer, stomach cancer, testicular cancer and skin cancer.

Examples of chronic infections include, but are not limited to, viral, bacterial, parasitic or fungal infections such as chronic hepatitis, lung infections, lower respiratory tract infections, bronchitis, influenza, pneumoniae and sexually transmitted diseases. Examples of viral infections include, but are not limited to, hepatitis (HAV, HBV, HCV), herpes simplex (HSV), herpes zoster, HPV, influenza (Flu), AIDS and AIDS related complex, chickenpox (varicella), common cold, cytomegalovirus (CMV) infection, smallpox (variola), colorado tick fever, dengue fever, ebola hemorrhagic fever, foot and mouth disease, lassa fever, measles, marburg hemorrhagic fever, infectious mononucleosis, mumps, norovirus, poliomyelitis, progressive multifocal leukencephalopathy (PML), rabies, rubella, SARS, viral encephalitis, viral gastroenteritis, viral meningitis, viral pneumonia, West Nile disease and yellow fever. Examples of bacterial infections include, but are not limited to, pneumonia, bacterial meningitis, cholera, diphtheria, tuberculosis, anthrax, botulism, brucellosis, campylobacteriosis, typhus, gonorrhea, listeriosis, lyme disease, rheumatic fever, pertussis (Whooping Cough), plague, salmonellosis, scarlet fever, shigellosis, syphilis, tetanus, trachoma, tularemia, typhoid fever, and urinary tract infections. Examples of parasitic infections include include, but are not limited to, malaria, leishmaniasis, trypanosomiasis, chagas disease, cryptosporidiosis, fascioliasis, filariasis, amebic infections, giardiasis, pinworm infection, schistosomiasis, taeniasis, toxoplasmosis, trichinellosis, and trypanosomiasis. Examples of fungal infections include, but are not limited to, candidiasis, aspergillosis, coccidioidomycosis, cryptococcosis, histoplasmosis and tinea pedis.

A BTLA antibody that blocks BTLA-HVEM interaction (e.g., BTLA8.2 or a derivative thereof) may be used as a vaccine adjuvant for the treatment of a cancer or a chronic infection.

The invention relates to a vaccine for the treatment of a cancer or a chronic infection comprising a BTLA antibody that blocks BTLA-HVEM interaction (e.g., BTLA8.2 or a derivative thereof).

The invention relates to a kit for the treatment of a cancer or a chronic infection comprising:
a) a BTLA antibody that blocks BTLA-HVEM interaction (e.g., BTLA8.2 or a derivative thereof); and
b) a vaccine for the treatment of a cancer or a chronic infection.

The two elements of the kit may be administered concomitantly or sequentially over time.

Examples of vaccine for the treatment of a cancer or a chronic infection are: include, but are not limited to vaccines against viral, bacterial, parasitic or fungal infections such as HIV and HBV and vaccines against viral associated cancers (for instance HPV or HBV) or anti cancer vaccines for instance used to treat patients with melanoma, leukemia, breast cancers, lung cancers.

The invention also relates to pharmaceutical composition comprising an antibody of the invention.

Therefore, an antibody of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semI-3889solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The invention will further be illustrated in view of the following figures and example.

EXAMPLE

Abstract

PD-1 and BTLA are receptors that negatively regulate T-cell activation. We have investigated their respective expression on human T cell subsets and their regulation following activation and finally compared their role in the regulation of T cell functions since there is no side by side comparison of their respective distribution and function. BTLA is expressed on naïve CD4 and CD8 T cells and its expression was down-regulated on Effector-type and Memory type $CD8^+$ T cells. In contrast, PD-1 was preferentially expressed by Effector and Memory type $CD4^+$ and $CD8^+$ T cells rather than Naive T cells. Engagement of PD-1 and/or BTLA by agonistic specific monoclonal antibodies blocked by the same strength CD3/CD28-mediated T cell proliferation and Th1 and Th2 cytokine secretion. However, blockade of PD-1 and/or BTLA engagement following allogenic stimulation of T cells by DCs, revealed a robust inhibitory effect of PD-1 as compared to BTLA and no additive effect was detected between the two molecules neither in weak (iDCs) nor in strong (mDCs) allostimulation. Indeed, PD-1 blockade resulted in memory-type T cell expansion and a major increase in cytokine secretion including IFNγ, TNF and IL-10. During acute CMV infection, BTLA was overexpressed on CMV specific T cells especially naïve and effector type cells and on memory and effector type cells after recovery from the CMV infection. We then monitored the CD8 response to CMV pp65 peptides, our results also demonstrated that PD-1 expression was up-regulated on CMV-specific $CD8^+$ T cells, while BTLA expression was in contrast down-regulated and in vitro blockade of PD-1 or BTLA pathway by anti-PD-1 or anti-BTLA antibodies was able to increase the CMV-specific $CD8^+$ T cell proliferation. Thus, our results indicate that like PD-1, BTLA also provides a target for enhancing the functional capacity of CTLs in viral infections. However, they differ in their role in the regulation of allogeneic stimulation and possibly transplantation.

Material and Methods
Generation of Anti-Human PD-L1, PD-L2, PD-1, BTLA and HVEM mAbs and Fab Fragmentation All mAbs were produced similarly. Female BALB/c mice were immunised by IP injection with 10 μg of human Ig fusion protein with 250 μl of Freund adjuvant. Immunisation was repeated three times at 2 weeks intervals, the fourth immunisation was made by IV injecting with 10 μg of Ig fusion protein (100 μl) in the codal tail. Three days later spleen cells were fused with X63Ag8 myeloma cells with PEG 1500 (Roche) and cloned with HAT selection (Sigma) and Hybridoma cloning factor (HCF from Origen). The hybridoma supernatants were screened by cell surface staining human PD1, PD-L1, PD-L2, BTLA or HVEM transfected COS cells line respectively and for lack of reactivity with untransfected COS cells. Anti-PD1 (PD1.3, IgG2b; PD1.6, IgG1), anti-PD-L1 (PD-L1.3, IgG1), anti-PD-L2 (PDL2.1, IgG1), anti-BTLA (BTLA6.4, IgG1; BTLA7.1, IgG2b; BTLA8.2, IgG1) and anti-HVEM (HVEM 8.5, IgG1) were selected as reagents for FACS analysis and functional studies. Fab fragments of blocking mAbs were generated and purified with the ImmunoPure Fab Preparation Kit following the manufacturer's recommendations (Pierce). Fragments were concentrated and washed into PBS on a Centricon-10 (Millipore). Protein purity was assessed by nonreducing SDS-PAGE, followed by detection with Coomassie blue. Protein concentration was determined by measurement of the absorbance at 280 nm Analysis by Flow Cytometry of PD-1 and BTLA Expression on T Cell Subsets and Activated T Cells Peripheral blood mononuclear cells (PBMC) were obtained from healthy donors and isolated by fractionation over Lymphoprep gradients (Abcys). To facilitate cell surface staining, mAbs to PD-1 (PD-1.3.1) and BTLA (BTLA7.1) were stained with Alexa Fluor 647 using a commercially available kit (Invitrogen). Briefly, PBMC were incubated with both the optimized dilution of the Alexa fluor 647-conjugated anti-PD-1 or anti-BTLA Abs and a corresponding lineage-specific mAb: anti-CD3 PC7, anti-CD4-Pacific Blue, anti-CD8-Alexa 700, anti-CD27-PE, and biotinylated anti-CD45RA (all from Becton Dickinson). The use of CD27 and CD45RA as surface markers allowed us to analyse PD-1 and BTLA expression on different $CD4^+$ and $CD8^+$ subsets: ($CD27^+CD45RA^+$: Naive (N), $CD27^+$ CD45RA and $CD27^-CD45RA^-$ Effectors-type T cells and $CD27^-CD45RA^+$: Effectors (E).

Dead cells were eliminated using LIVE/DEAD Fixable Dead Cell Stain Kit (Invitrogen). Cells were washed twice in cold PBS with 2% FCS and 0.02% sodium azide, fixed in 4% paraformaldehyde and analyzed on FACS Aria flow cytometer (BD Immunocytometry Systems). To analyse PD-1 and BTLA co-expression, we used the same protocole with Alexa fluor 647-conjugated anti-PD-1 and Alexa fluor 488-conjugated anti-BTLA in combination with a corresponding lineage-specific mAbs.

Expression of PD-1 and BTLA on CMV-$CD8^+$ T cells was performed using phycoerythrin (PE) HLA-A*0201 CMV pp65 (NLVPMVATV)MHC tetramers (iTAg™, Beckman Coulter Immunotech)

For T cell expression kinetics of PD-1 and BTLA, $CD4^+$ and $CD8^+$ T cells were isolated from PBMC by T cell negative isolation Kit (Miltenyi Biotec) and cultured in RPMI 1640 supplemented with 10% FCS (GIBCO). $CD4^+$ or $CD8^+$ T cells ($1.5 \times 10^5$ cells/well) were activated in 96-well, flat-bottom plates (Costar, Cambridge, Mass.) coated with 1 μg/ml anti-CD3 (OKT3) and 2 μg/ml of soluble anti-CD28 (CD28.2); cells were harvested each day for FACS analysis using Alexa fluor 647-conjugated anti-PD-1 and anti-BTLA. CD25 expression was used as activation control.

Artificial APC (aAPC) Confection and T Cell Assays

Human $CD4^+$ and $CD8^+$ T cells were purified by negative selection from peripheral blood mononuclear cells using magnetic beads (Miltenyi Biotec) and were routinely more than 97% $CD3^+$, more than 98% $CD4^+$ for $CD4^+$ T cell isolation and more than 95% $CD8^+$ for $CD8^+$ T cell isolation as determined by flow cytometry. T cells were stimulated with aAPC at a ratio of 3:1 (cells to beads) comprised of magnetic beads (Dynabeads M-450 Epoxy, Dynal Biotech) coated with the following Abs: anti-CD3 (OKT3), anti-human CD28 (CD28.2), anti-human PD-1 (PD-1.6.4), anti-human BTLA (BTLA6.4) and anti-MHC class I (MHC I) (YJ4). As previously described (28), these aAPCs were coated with suboptimal anti-CD3 Ab (5%), suboptimal levels of anti-CD28 Ab (10%), and either anti-MHC class I Ab (CD3/28/MHC I), anti-PD-1 Ab (CD3/28/PD-1+CMH I), anti-BTLA Ab (CD3/28/BTLA+CMH I) or anti-PD-1+ anti-BTLA (CD3/28/PD-1+BTLA), constituting the remaining 85% of protein added to the bead. T cells ($1.5 \times 10^5$ cells/well) were stimulated in round-bottom 96-well. Supernatants were harvested at 48 h to analyse cytokine secretion by human Th1/Th2 cytokine Kit (BD™ Cytometric Bead Array). Proliferation was measured at day 5 by tritiated thymidine incorporation for the last 18 h.

Blockade of PD-1-PD-L and BTLA-HVEM Binding

Competitive binding experiments were performed to test the binding blockade effect of our mAbs. COS 7 cells transfected to express PD-L1 or PD-L2 were preincubated with anti-PD-L1 (PD-L1.3.1) or anti-PD-L2 (PD-L2) respectively, followed by the addition of PD-1-Ig. Cells were washed twice, incubated with goat anti-human-PE, washed again, fixed with 2% paraformaldehyde, and analyzed on FACScan. Cells incubated with PD-1-Ig and mouse IgG, or mouse IgG with no PD-1-Ig were used as positive and negative controls, respectively. Similarly, PD-1 transfected COS 7 cells were preincubated with anti-PD-1 (PD-1.3.1) or mouse IgG control, followed by the addition of PD-L1-Ig or PD-L2-Ig. Anti-PD-1 blockade effect was then evaluated by flow cytometry using goat anti-human-PE. Blockade of BTLA-HVEM interaction were determined by two procedures: the first by using anti-BTLA (BTLA8.2) to block the interaction of HVEM-Ig with BTLA transfectant cells, and the second by using anti-HVEM (HVEM8.5) that blocks specifically BTLA-HVEM but not LIGHT-HVEM interaction.

Preparation of Monocyte-Derived DCs

Peripheral blood mononuclear cells were obtained from healthy donors and isolated by Lymphoprep (AbCys) density gradient centrifugation. CD14$^+$ monocytes were then immunomagnetically purified with CD14 mAb-conjugated microbeads (Milteniy Biotec). Purity of the CD14$^+$ cells by flow cytometry analysis was >98%. For generation of monocyte-derived DC (Mo-DC), CD14$^4$ monocytes were cultured for 5 days in 6-well plates at 2×10$^6$ cells/well (Falcon; BD Biosciences) in RPMI 1640 medium containing 10% FCS (GIBCO) and supplemented on days 0, 3 and 5 with 100 ng/ml GM-CSF (AbCys) and 20 ng/ml IL-4 (AbCys). Immature DCs were harvested at day 5 and their maturation was accomplished by coculturing them for 2 days with 50-Gy-irradiated CD40L-transfected cells (2.10$^5$/well).

CFSE Labelling and Allogenic Stimulation of T Cells with Monocyte-Derived DCs

T cells were isolated from peripheral blood with a Pan T-negative isolation kit (Miltenyi Biotec) according to the manufacturer's protocol. CD3$^+$ T cells were routinely >97% pure. T cells were labelled with 0.5 µM CFSE (carboxyfluorescein diacetate, succinimidyl ester) (Invitrogen) for 10 min at 37° C., washed and cultured (2.10$^5$/well) with immature, or mature allogenic DCs (2×10$^4$/well) in triplicate in 96-well flat-bottom plates (Falcon; BD Biosciences) in RPMI 1640 medium containing 10% FCS in the presence of blocking Fabs to PD-L1 (PD-L1.3.1), PD-L2 (PD-L2), PD-1 (PD-1.3.1), BTLA (BTLA8.2) and HVEM (HVEM8.5) or isotype Fab controls. Cultures were incubated for 5 days and then proliferation of CFSE labelled CD4$^+$ and CD8$^+$ T cells were measured by flow cytometry (FACS Canto, Beckman Coulter). Proliferation also was measured on different T cell subsets using CD27 and CD45RA as cell surface markers.

ELISA for Cytokine Analysis

To determine the production of cytokines, cell-free supernatants were collected at 96 h and assayed for IL-2, IL-10, IFNγ, and TNF by ELISA using OptEIA kits (BD Pharmingen) according to the manufacturer's instructions.

Induction of Specific Anti-pp65 CD8$^+$ T Cells

The iDCs and mature DCs were pulsed for 2 h at 37° C. in RPMI 1% FCS with a 10 µg/ml CMV pp65 NLVPMVATV peptide. After two washes, peptide-pulsed DCs (2×10$^4$/well) were cultured with autologous CFSE labelled-T cells (2×10$^5$/well) in the presence of anti-PD-1, anti-BTLA blocking mAbs or isotype control. On day 7, T cells were harvested and restimulated with 10 µg/ml of CMV pp65 NLVPMVATV peptide for 6 hours. Proliferation was measured by CFSE dilution.

Statistical Analysis

All data were analysed using GraphPad Prism version 4.00 for Windows, GraphPad Software. The Wilcoxon matched pairs test was utilized to compare BTLA expression on matched CD4$^+$ and CD8$^+$ T cells. Kruskal-Wallis ANOVA was used to examine the variation of PD-1 and BTLA expression on CD4$^+$ and CD8$^+$ T cell subsets. The Mann-Whitney U test was utilized to determine significance of differences between anti-PD-1, anti-BTLA and matched isotype controls effect. Differences were considered as statistically significant when P<0.05.

Results

PD-1 and BTLA are differently expressed on CD4$^+$ and CD8$^+$ T lymphocytes

We first performed the side by side investigation of the expression of PD-1 and BTLA on human T cell subsets in the peripheral blood of healthy individuals using CD27 and CD45RA as cell surface markers (FIG. 1A).

We found a very low expression of PD-1 on both CD4$^+$ and CD8$^+$ T cells, whereas, BTLA was readily expressed on T lymphocytes at higher levels than PD-1. We observed mean fluorescence intensity values of for PD-1 and for BTLA in normal individuals. Our results demonstrated an identical expression of PD-1 between CD4$^+$ and CD8$^+$ cells. In contrast, BTLA was more expressed on CD4$^+$ then CD8$^+$ T cells (p=0.0005) (FIG. 1B). Using CD27 and CD45RA markers, we have dissociated CD8$^+$ T cells in four subsets (Naives (N) CD27+/CD45RA+, Effector Memory (EM) CD27−/CD45RA−, Central Memory (CM) CD27+/CD45RA− and Effector (E) CD27−/CD45RA+). CD4 cells were defined has naïve or memory type.

Comparing expression of PD-1 and BTLA, we found a very low expression of PD-1 on Naive CD4$^+$ T cells and a highly significant up-regulation on Effector (p<0.001), and Effector Memory (p<0.001) CD4$^+$ T cells. However, no change was detected in the expression of BTLA on different CD4$^+$ subsets. On CD8$^+$ T cells, in addition to significant up-regulation of PD-1 on Effector and Effector Memory T cells (p<0.001), we found also a significant up-regulation on Central Memory cells (p<0.01). In contrast, BTLA demonstrated a significant down-regulation on Effector (p<0.001), Effector memory (p<0.01) and Central Memory CD8$^+$ T cells (p<0.05) as compared to Naive CD8$^+$ T cells (FIG. 1B).

Finally we evaluated the co-expression of PD-1 and BTLA on different T lymphocyte subsets. Except Naive T cells which express only BTLA, it appears that PD-1 and BTLA expression are completely dissociated on Effector CD8$^+$ T cells. In contrast, high co-expression was detected on Effector CD4$^+$ T cells indicating a strong inhibitory effect of these molecules on this small sub-population.

Unlike BTLA which is constitutively expressed on CD4$^+$ and CD8$^+$ T cells, the expression of PD-1 is low on resting T cells. PD-1 is up-regulated on activated CD4$^+$ and CD8$^+$ T lymphocytes and the maximal expression is observed after 48 h.

Previous reports have shown that BTLA expression decreases on CD4$^+$ and CD8$^+$ T cells stimulated with anti-CD3 and anti-CD28 mAbs. In our experiments, purified CD4$^+$ and CD8$^+$ T cells were stimulated with anti-CD3 and anti-CD28 and harvested each day for FACS analysis. Unstimulated T cells expressed low level of PD-1 whereas BTLA was 4 fold more expressed than PD-1 on both CD4$^+$ and CD8$^+$ T cells. CD8$^+$ T cells showed late and very low increase in PD-1 expression. In contrast, CD4$^+$ T cells demonstrated early and a progressive increase in the intensity of PD-1 expression (FIG. 5).

CD8$^+$ T cells both demonstrated a progressive decrease in the intensity of BTLA expression. The level of BTLA expression diminished at 48 h in CD8$^+$ T cells, and then there is a progressive increase to reach the initial resting levels expression at 96 h (FIG. 5).

PD-1 and BTLA are Potent Inhibitors of CD3/CD28-Mediated Costimulation

Previous studies have described agonistic anti-human PD-1 and anti-human BTLA (Bennett et al., J. Immunol., 2003, 170, 711-8; Chemnitz et al., J. Immunol., 2004, 173, 945-54). PD-1 engagement results in the inhibition of T cell expansion and CD28-mediated up-regulation of IL-2, IL-10, IL-13, IFNγ and Bcl-x$_L$ transcripts in primary purified CD4$^+$ T cells. However, the relative efficiency of both systems and their potential cooperation has not been investigated. To investigate whether PD-1 and BTLA exert a functional cooperation on T cell inhibition we used artificial antigen presenting cells (aAPC), purified CD4$^+$ or CD8$^+$ T cells were stimulated with aAPC (3 cells: 1 aAPC) coated with: anti-CD3 (OKT3) and anti-human CD28 (28.2) together with anti-human PD-1 (PD1.6.4), anti-human BTLA (BTLA6.4) or both and anti-MHC class I (YJ4). For most experiments, these aAPCs were coated with suboptimal anti-CD3 Ab (5%), suboptimal levels of anti-CD28 Ab (10%) (Riley et al., Proc. Natl. Acad. Sci. USA, 2002, 99, 11790-5). Stimulation of primary human CD4+ or CD8+ T cells with anti-CD3-, anti-CD28-, and anti-MHC class I (designated MHC I)-coated beads for 5 days leads to robust T-cell proliferation and IL-2 production. In contrast, PD-1+ MHC I and BTLA+MHC I aAPCs inhibited similarly and significantly both CD4+ and CD8+ T cells proliferation-CD3/CD28 induced. The inhibitory effect of PD-1 or BTLA alone was very strong and no additive or synergistic effect was detected between the two molecules in these conditions (FIG. 2A). To confirm these results, we tried to evaluate the inhibitory effect of PD-1 and/or BTLA using high CD3/CD8-mediated T cell costimulation. In optimal condition of activation, no inhibition was detected even with anti-PD-1 and anti-BTLA together (data not shown) indicating that PD-1 and BTLA inhibit by the same strength only sub-optimal CD3/CD28 mediated activation.

Both PD-1 and BTLA inhibited CD3 and CD28-mediated up-regulation of IL-2, IFNγ, and TNF by CD4+ T cells (FIG. 2A) and CD8+ T cells (FIG. 2A). IL-4 and IL-5 were also strongly inhibited by PD-1 and BTLA engagement on both CD4+ and CD8+ T cells (data not shown).

Using sub-optimal conditions of T cell activation, PD-1 and BTLA mAbs inhibited strongly T cell proliferation and Th1/Th2 cytokines secretion and no functional cooperation was detected between the two molecules.

PD-1 is More Involved than BTLA in Regulating Allogenic Stimulation of CD4+ and CD8+ T Cells by DC.

We next investigated the role of PD-1 and BTLA using allogeneic stimulation, a condition where their ligands PD-L1, PD-L2 and HVEM respectively, are expressed. We evaluated the functions of PD-1, BTLA or PD-1 and BTLA using mAbs that block PD-1 PD-L interaction and BTLA-HVEM binding in T cells allogeneic responses against dendritic cells of week (iDC) vs strong (mDC) stimulatory capacity.

To analyse both CD4+ and CD8+ T cells, CFSE-labelled T cells were cultured with allogenic iDCs or mDCs in the presence of blocking Fab specific to PD-L1, PD-L2, PD-1 and BTLA or matched isotype Fab controls. Five days later, cells were harvested and labelled with CD27 and CD45RA to analyse different T cell subsets proliferation by CFSE dilution. We first compared the percentage of different subsets in the presence of blocking Fabs or isotype Fab controls. Interestingly, using weak allostimulation (iDCs), blockade of PD-1/PD-L interaction by anti-PD-L1 and anti-PD-L2 together or anti-PD-1 led to highly significant enrichment in Effector CD4+ but not CD8+ T cells. Blockade of BTLA engagement by anti-BTLA also led to significant increase in the percentage of Effector CD4+ T cells. No significant additive effect was detected between PD-1 and BTLA (FIG. 2B). Then, we compared the proliferation of allogenic T cells against iDCs. Anti-PD-1 Fab and nti-PD-L1+anti-PD-L2 together resulted in 4-fold increase in CD8+ T cell proliferation (FIG. 2B) with 3 fold increase in Central (p=0.0068) and Effector memory (p=0.017) CD8+ T cells (FIG. 2B). No additive effect was detected with anti-PD-1 and anti-BTLA together. Anti-PD-1 blockade as well as anti-PD-L1+anti-PD-L2 blockade resulted in similar increase in Central Memory and Effector Memory CD8+ T cells proliferation.

Similar results were found with CD4+ T cells. As shown in FIG. 2C, mDCs stimulated a robust allogeneic response. Anti-PD-1 Fab, like anti-PD-L1 and anti-PD-L2 Fabs together resulted in 2 fold increase in CD4+ T cell proliferation with a strong increase (5-fold) in CD4+ T cells with surprisingly a membrane phenotype CD45RA+CD27+Naive phenotype as well as Memory T cells. The effect of PD-1 blockade was less dramatic on CD8+ than with iDCs (data not shown). The treatment of mDC with anti-BTLA showed no significant increase of CD4+ or CD8+ T cell proliferation compared with that of cultures treated with an isotype control. Finally, combination of anti-PD-1 and anti-BTLA showed no additive effect.

The effect of PD-1 and/or BTLA blockade on cytokine secretion was examined. PD-1/PD-L interaction blockade using anti-PD-1 or anti-PD-L1 and anti-PD-L2 Fabs together resulted in highly significant increase in IFNγ and TNF secretion following iDCs stimulation and a lesser extent mDCs (FIGS. 2B and 2C) Inhibition of BTLA/HVEM interaction using anti-BTLA Fab showed a weak but significant increase in IFNγ and TNF secretion using iDCs and mDCs. Similar results were obtained using anti-HVEM Fab that specifically blocks BTLA/HVEM but not LIGHT/HVEM interaction confirming the previous observations with anti-BTLA blockade (FIGS. 2B and 2C).

In all experiments, blockade effect of PD-1/PD-L interaction on T cell proliferation and cytokine secretion was similar between anti-PD-1 and anti-PD-L1 and anti-PD-L2 Fabs together, indicating that PD-L1 and PD-L2 could be the only two ligands for PD-1 on DCs.

BTLA is Expressed on CD8 T Cells Specific of CMV and EBV Virus During Acute Viral Infection We have tested the expression of BTLA on CMV specific T cells during reactivation of CMV during the course of kidney transplantation (FIG. 3). BTLA is overexpressed in CMV specific T cells during the acute phase of the infection in naïve but also effector type cells (EMRA). After recovery, BTLA expression decreases and returns to baseline levels except on memory and EMRA cells. As controls we used the activation antigen HLA-DR that was also upregulated and indicated the activation status of the anti-viral specific T cells. An additional marker was evaluated, PD-1 that proved to be upregulated on activated antiviral specific T cells on naive as well as memory T cells.

This observation indicates that BTLA is overexpressed on CMV specific cells during acute infection and remains elevated on memory cells after recovery.

PD-1 or BTLA Pathway Blockade Enhances CMV-Specific CD8+ T Cell Proliferation

Recent evidence from lymphocytic choriomeningitis virus (LCMV) infection in mice, HIV and HCV infection in humans indicates a crucial role for PD-1 pathway in virus-specific CD8+ T cells exhaustion and T cell dysfunction during chronic infection (Barber et al., Nature, 2006, 439, 682-7; Petrovas et al., J. Exp. MEd., 2006, 203, 2281-92). In our study, we first compared the expression of PD-1 and BTLA in CMV-virus-specific CD8+ T cells. We found an up-regulation of PD-1 expression on tetramer-positive (tetramer+) CD8+ T cells specific for CMV as compared to tetramer-negative (tetramer−) CD8+ T cells. BTLA in contrast, was down-regulated on tetramer-positive CD8+ T cells (FIG. 4). To address the potential role of PD-1 or BTLA pathways in the activation of CMV specific CD8+ T cells we then compared the effect of PD-1 or BTLA pathway on CMV-specific CD8+ T cell proliferation using blocking anti-PD-1 or anti-BTLA in autologous co-culture of T cells with DCs pulsed with pp65 peptide CMV. DCs of weak (iDCs) vs strong (mDCs) stimulatory capacity were used and T cell proliferation were measured by CFSE dilution. Unlike what we observed in allogenic stimulation of T cells, Anti-PD-1 or anti-BTLA blocking antibodies enhanced pp65-specific CD8+ T cell proliferation to the similar extent suggesting a potential role of these molecules in restoring CTLs functions (FIG. 4). The enhancement was generally greatest with the weaker DC populations (iDC) than with the mDC.

These data indicate that the cosignaling molecule BTLA is expressed during infection and is involved in the inhibition of anti viral T cell function.

REFERENCES

Throughout this application, various references describe the state of the art to which this invention pertains. The disclosures of these references are hereby incorporated by reference into the present disclosure.

The invention claimed is:

1. An anti-BTLA antibody comprising the CDRs of the heavy chain variable region and the light chain variable region of the anti-BTLA antibody which is obtainable from the hybridoma accessible under CNCM deposit number I-4123.

2. The anti-BTLA antibody according to claim 1, wherein said antibody is the anti-BTLA antibody which is obtainable from the hybridoma accessible under CNCM deposit number I-4123 or a Fab or F(ab')$_2$ fragment thereof.

3. A hybridoma accessible under CNCM deposit number I-4123.

4. A method for treating cancer in a human or animal body in need thereof, comprising the administration of a therapeutically effective amount of an anti-BTLA antibody according to claim 1 to said human or animal body.

* * * * *